United States Patent [19]
Rudnick

[11] Patent Number: 5,320,639
[45] Date of Patent: Jun. 14, 1994

[54] VASCULAR PLUG DELIVERY SYSTEM

[75] Inventor: James J. Rudnick, Waldwick, N.J.

[73] Assignee: Meadox Medicals, Inc., Oakland, N.J.

[21] Appl. No.: 30,660

[22] Filed: Mar. 12, 1993

[51] Int. Cl.⁵ .............................................. A61B 17/04
[52] U.S. Cl. ...................................... 606/213; 604/15; 604/51; 606/228
[58] Field of Search ........ 606/213, 215, 216, 228–232; 604/13, 15, 51, 60, 158

[56] References Cited

U.S. PATENT DOCUMENTS

| | | | |
|---|---|---|---|
| 4,536,178 | 8/1985 | Lichstein et al. | 604/15 |
| 4,650,459 | 3/1987 | Sheldon | 604/15 |
| 4,852,568 | 8/1989 | Kensey | 606/213 |
| 5,192,300 | 3/1993 | Fowler | 606/213 |
| 5,192,302 | 3/1993 | Kensey et al. | 606/213 |
| 5,221,259 | 6/1993 | Weldon et al. | 606/213 X |

OTHER PUBLICATIONS

A. Merino, C. Faulkner, A. Corvalan and T. Sanborn, *Percutaneous Vascular Hemostasis Device For Interventional Procedures*, in Catheterization and Cardiovascular Diagnosis, 319–22 (Wiley-Liss, Inc. 1992).

*Primary Examiner*—Peter A. Aschenbrenner
*Attorney, Agent, or Firm*—Hoffmann & Baron

[57] ABSTRACT

A vascular plug delivery system for in vivo delivery of a vascular plug to the site of a puncture in a blood vessel. The device utilizes flashback to ensure that the plug is properly positioned adjacent the puncture prior to delivery of such plug, thereby ensuring complete hemostasis of the puncture.

31 Claims, 13 Drawing Sheets

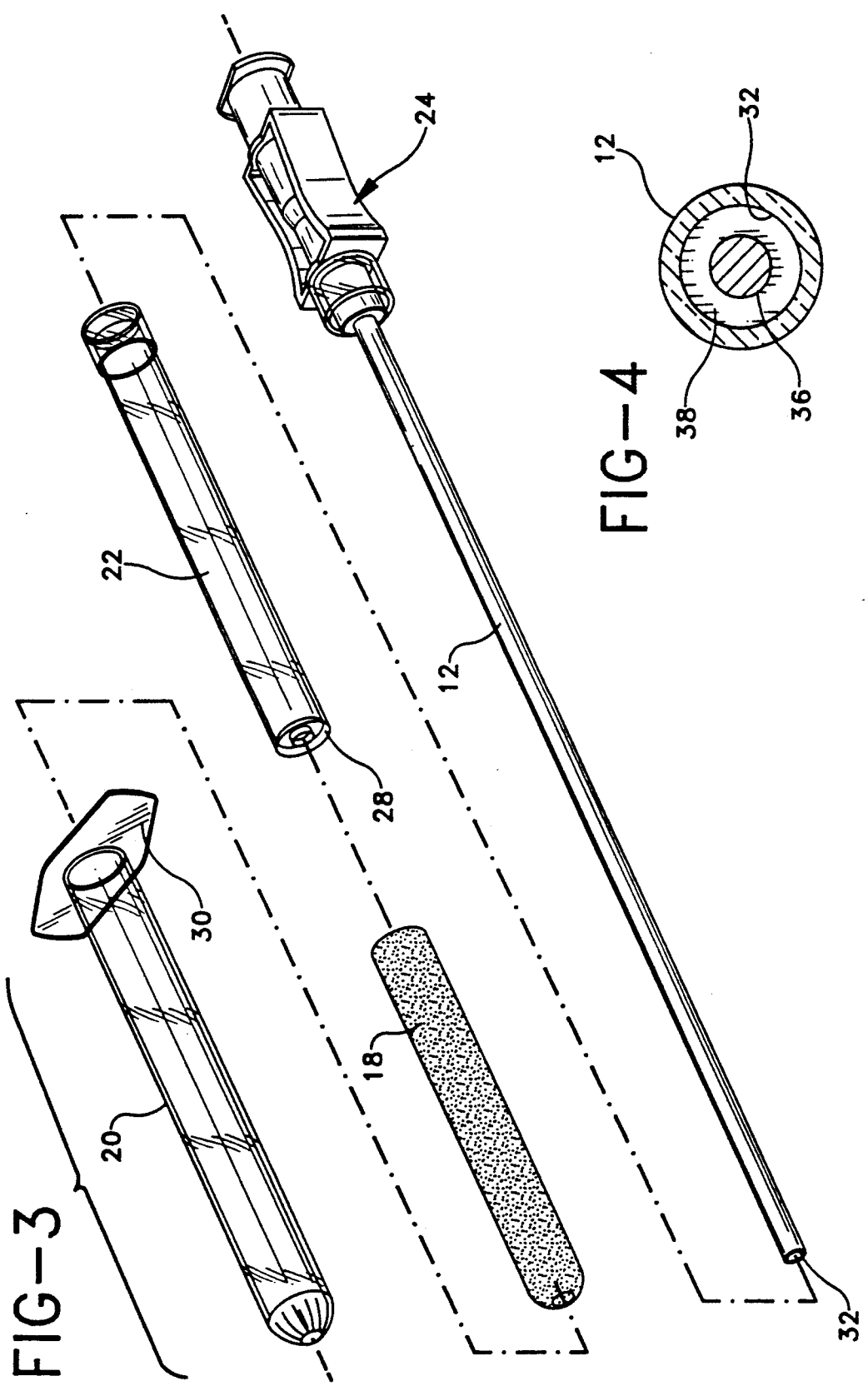

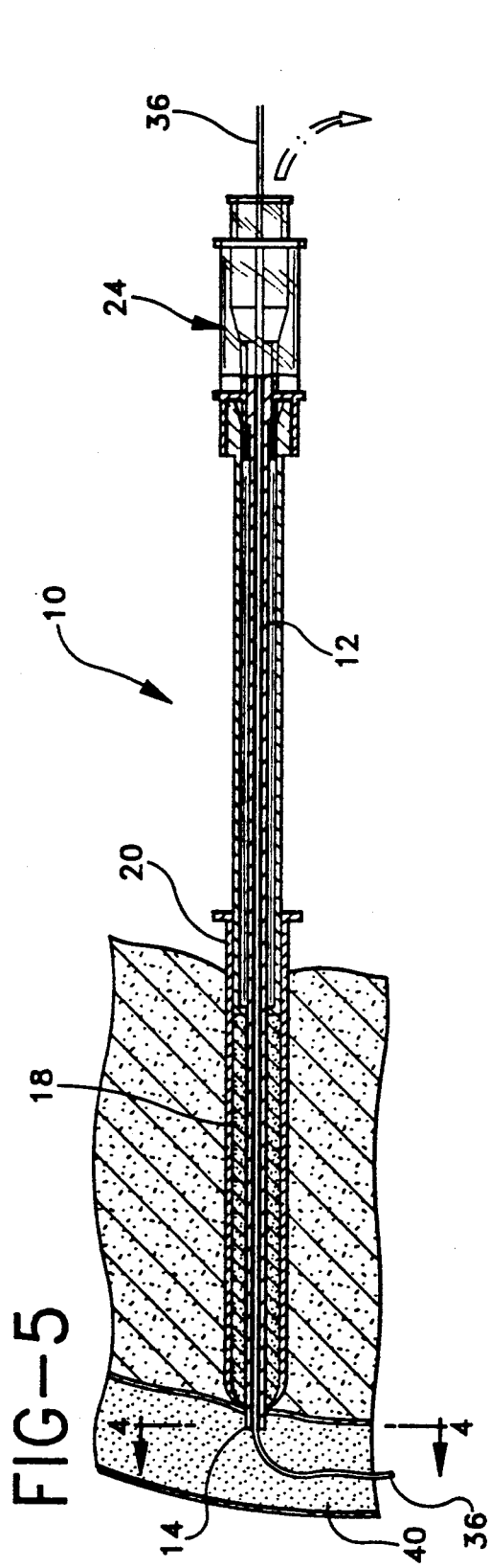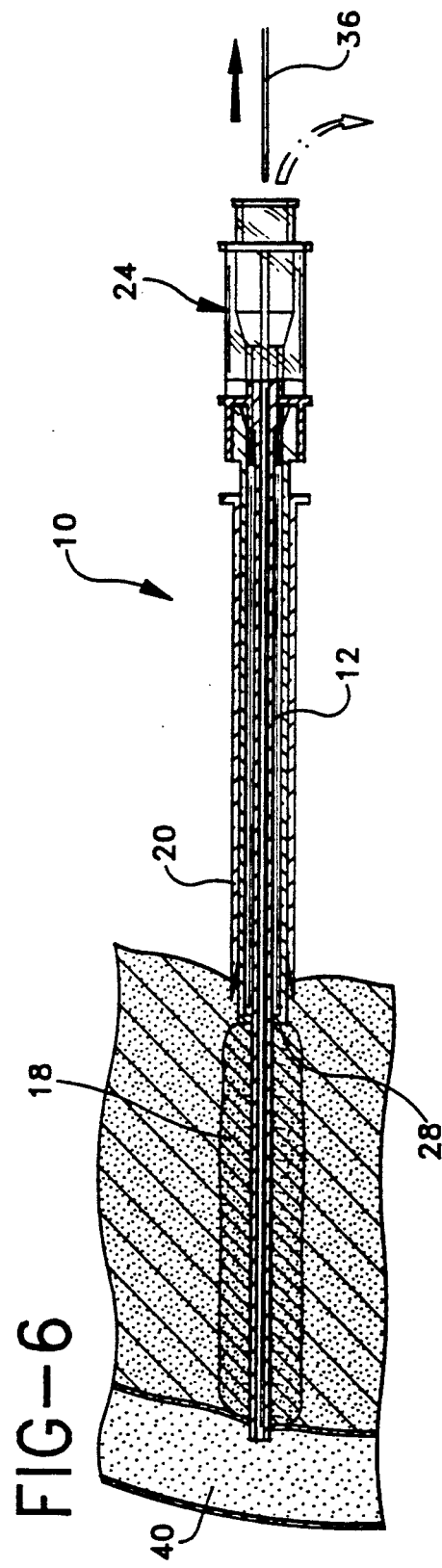

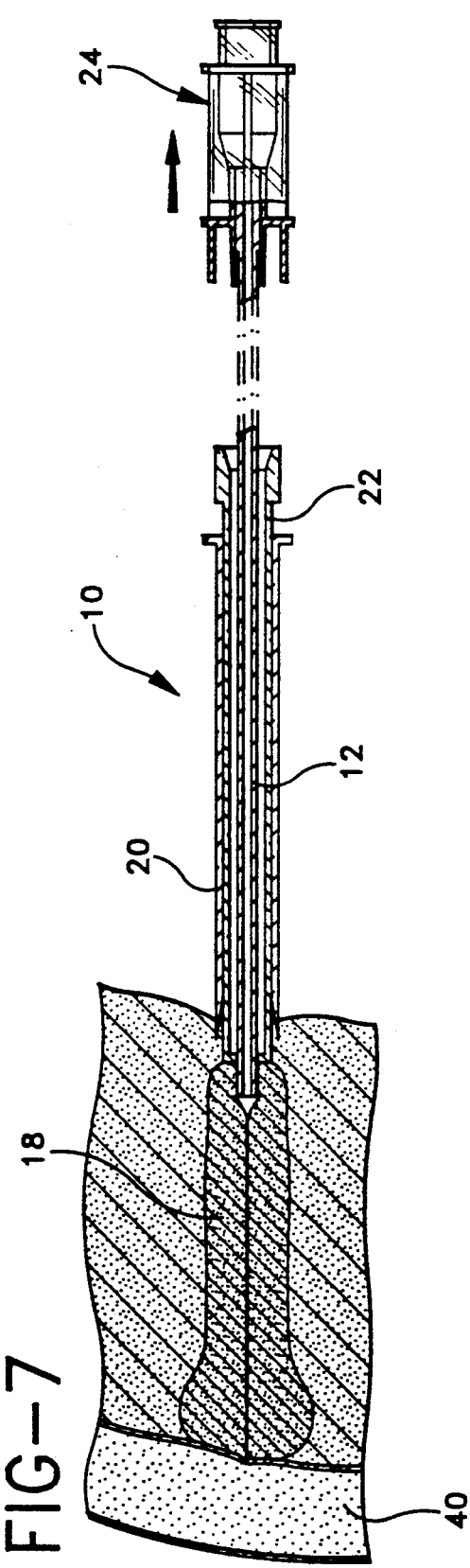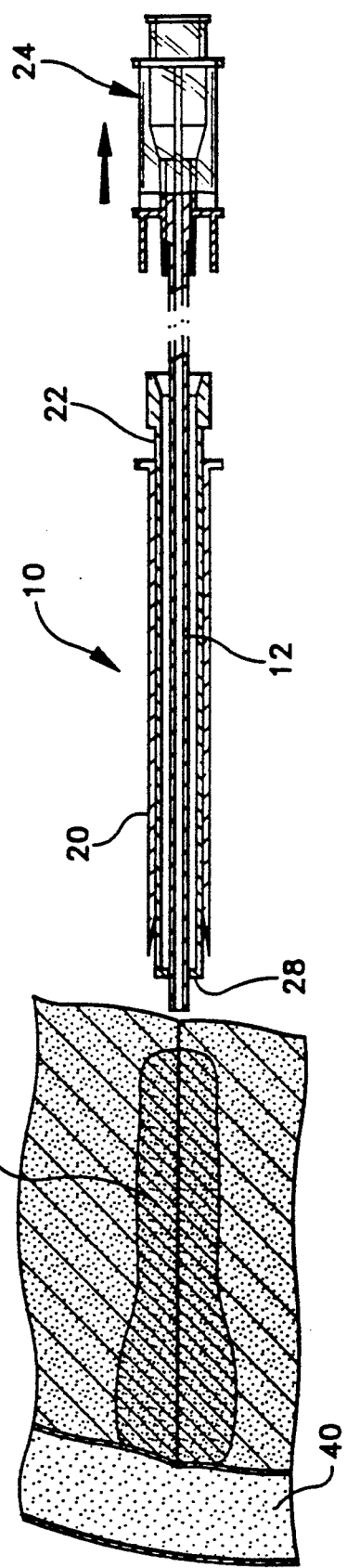

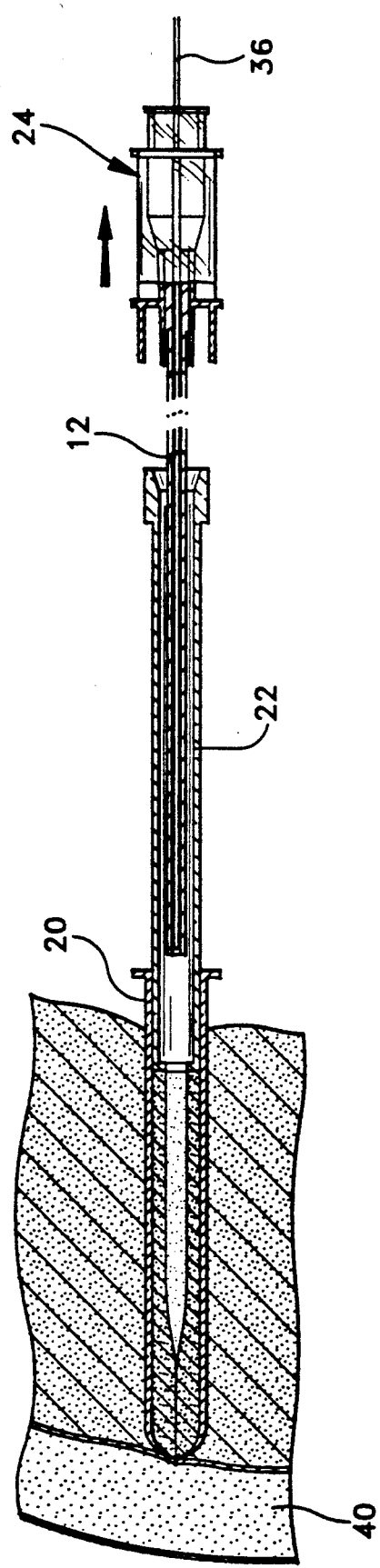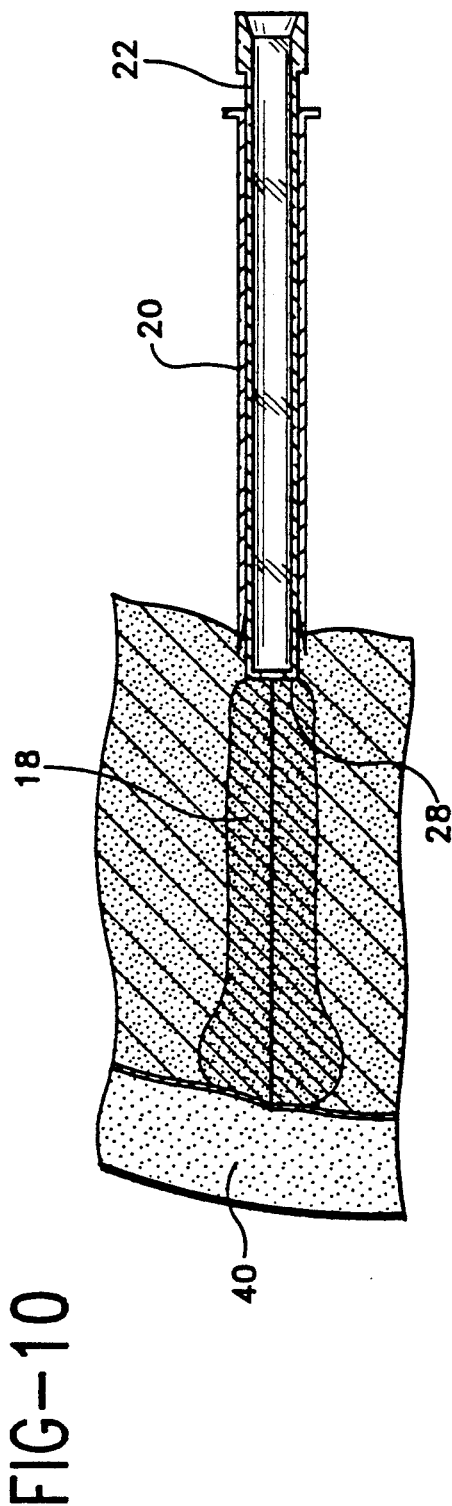
FIG-9
FIG-10

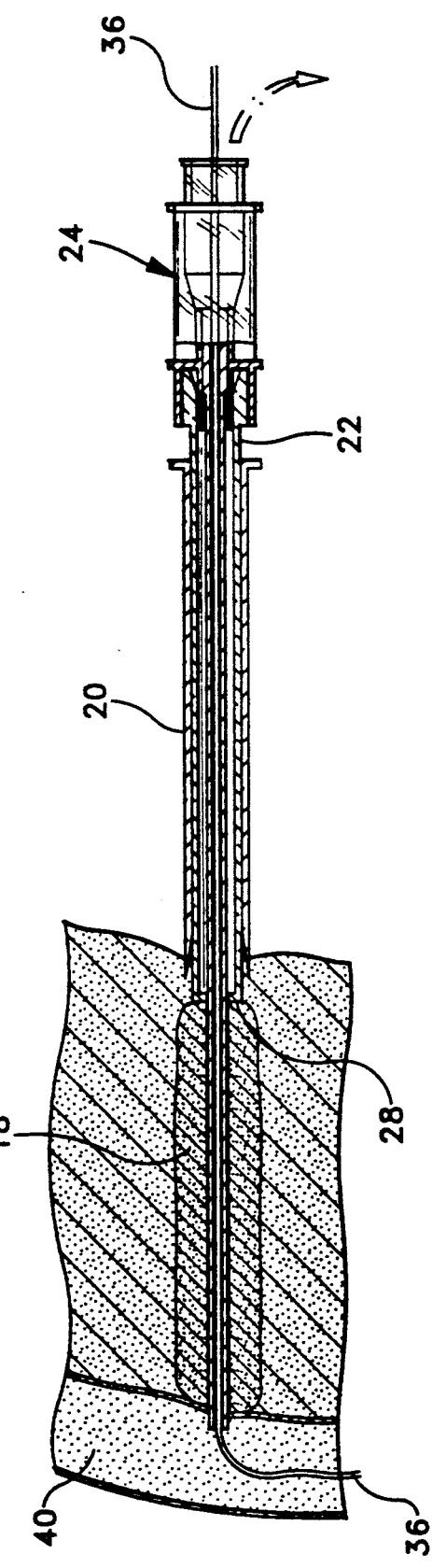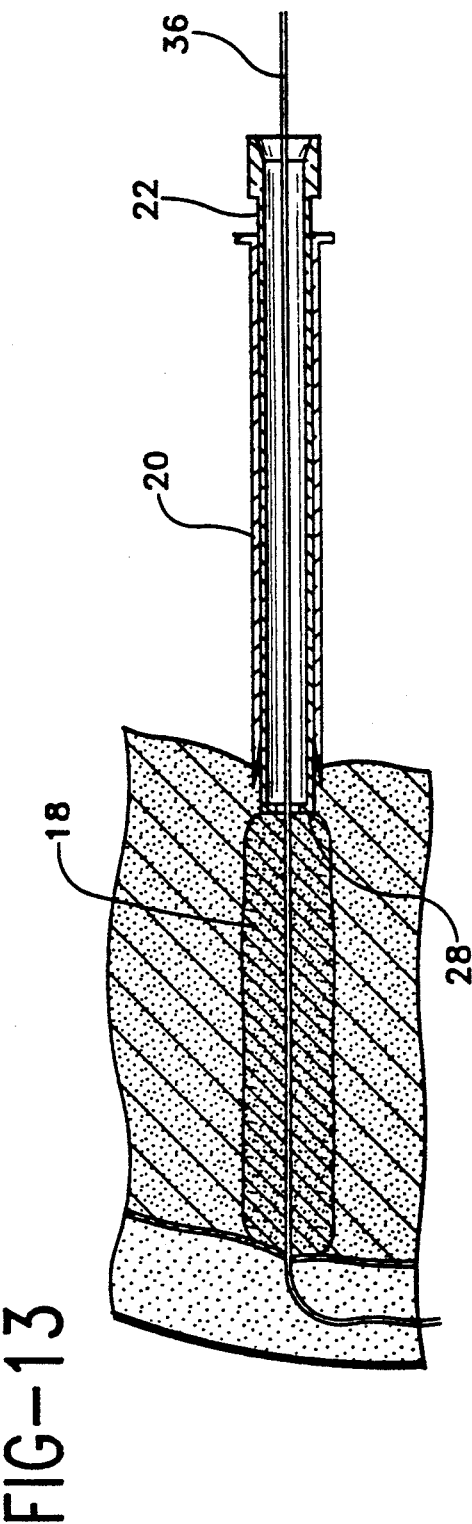

VASCULAR PLUG DELIVERY SYSTEM

BACKGROUND OF THE INVENTION

The present invention relates to a vascular plug delivery system and, more particularly, to a device and method for in vivo delivery of a vascular plug to the site of a puncture in a blood vessel.

Various medical procedures require a physician to insert and advance a catheter or similar device into a patient's blood vessel. Typically, the blood vessel is first punctured with a needle. Thereafter, a guidewire is advanced through the puncture into the vessel. A dilator may or may not be employed to expand the size of the puncture in the vessel. Next, the catheter is advanced over the guidewire and into the blood vessel. The physician then performs the necessary medical procedure and withdraws the catheter, guidewire, etc. from the patient.

Following the withdrawal of the catheter (or similar device) from the patient's blood vessel, it is necessary to control the bleeding until the puncture has clotted. The most common method for controlling this bleeding involves having a nurse or other trained professional apply direct compression to the site of the puncture. Such a technique, however, is not without risk. Applying too much pressure can result in a decrease of blood circulation to distal limbs, while too little pressure leads to bleeding that may create hematomas or aneurysms. Moreover, the compression technique is very time consuming (averaging ¼ hour to 1 hour) and, hence, expensive.

The prior art has suggested several alternative techniques for controlling the flow of blood following a catheterization procedure. For example, U.S. Pat. Nos. 4,744,364 and 4,852,568 disclose a method whereby a tubular body is inserted through the puncture following catheterization and an expandable plug is dispensed from the tubular body into the vessel and pulled taught against the interior wall of the vessel. The method, however, carries with it the inherent risks associated with introducing foreign objects into the blood vessel and, in addition, may prove difficult when deploying a closure in a relatively small-sized vessel. Further, it is difficult to ensure that the physician will be able to relocate the puncture in the vessel when introducing the tubular body (the guidewire having already been withdrawn).

Next, the Datascope Corporation of Montvale, N.J. has introduced a device called Vasoseal for sealing vascular punctures. The physician, at the beginning of the procedure, calculates the distance between the skin surface and the arterial surface. After the catheterization procedure, the physician chooses a plug system having a length corresponding to the original calculation and, thereafter, inserts a bottom and top plug into the tissue channel. However, because of various factors that may occur during the catheterization procedure (e.g., swelling of the local area) the initial length calculation performed by the physician may no longer be accurate. In addition, because only the tissue channel is guiding the plugs to the puncture, it is difficult to ensure that the plugs are, in fact, positioned at the puncture.

An additional technique is disclosed in U.S. Pat. No. 5,108,421, which relates to an assembly for position-ing a plug into a tissue channel. The assembly includes a catheter sheath, which is first inserted through the puncture in the blood vessel. A balloon catheter is then inserted through the sheath and, thereafter, the sheath is removed. Next, the balloon is inflated inside the vessel such that the balloon presses against the interior wall of the vessel at the puncture site. A plug is thereafter inserted into the tissue channel until the distal end of such plug contacts the balloon. The balloon is then deflated and the catheter removed. The technique, although minimizing the likelihood of delivering the plug into the vessel, includes the step of inflating a balloon in the vessel, a procedure which involves decreasing the circulation of blood through the vessel. In addition, because the balloon catheter is still deployed in the vessel at the time the plug is inserted, it is difficult to ensure that the entire puncture site will be covered by the plug after the catheter is withdrawn.

Finally, European Patent Application No. 476,178 A1 discloses a device for placing a plug at the site of a puncture in a blood vessel. The device includes a tube arrangement that may be advanced over a previously-positioned guidewire. After the tube contacts the wall of the vessel, the guidewire is withdrawn. A plug is then advanced through the tube arrangement to the puncture site. Because the guidewire has been withdrawn, it is difficult to ensure that the tube is still properly located at the puncture site at the time of delivery (e.g., the tube may have shifted during withdrawal of the guidewire or during insertion of the plug). In addition, the device provides no independent means for informing the physician that the tube arrangement has been completely advanced to the puncture site. Stated differently, in placing the plug, the physician is forced to rely only on the tactile sensation provided by the tube arrangement contacting the outer wall of the vessel, thereby introducing the possibility that the physician will advance the tube arrangement into the puncture and actually deliver the plug in the vessel itself or, alternatively, will not advance the tube arrangement far enough, which will deliver the plug a distance away from the puncture and allow bleeding from the vessel.

In light of the prior art, it would be desirable to provide a device for accurately and consistently delivering a vascular plug to the site of a puncture in a blood vessel, thereby ensuring complete hemostasis of the arterial puncture. This delivery should be accomplished with minimum additional intrusion to the blood vessel itself.

SUMMARY OF THE INVENTION

The present invention, which addresses the needs of the prior art, provides a device for in vivo delivery of a vascular plug to a site of a puncture in a blood vessel in which a guidewire has been inserted. The device includes a cannula capable of passing over a guidewire and which has sufficient length and dimension to enter a blood vessel puncture. The device also includes means for securing a plug in a delivery position over the cannula during introduction of the device. Finally, the device includes means for retaining the plug at a vessel puncture site during withdrawal of the cannula and the guidewire.

An alternative embodiment of the present invention provides a device having a cannula capable of passing over a guidewire and which has sufficient length and dimension to enter a blood vessel puncture. This device includes a housing adapted to slide over the cannula and which has sufficient space therein to accommodate a vascular plug disposed in a delivery position over the outside diameter of the cannula. Finally, this device includes means for retaining the plug at a vessel puncture site during withdrawal of the housing, the cannula and the guidewire from the puncture site.

The present invention also provides a method for in vivo delivery of a vascular plug to a site of a puncture in a blood vessel. The method includes the step of advancing a cannula having a plug disposed over its outside diameter to a vessel puncture site over a guide-wire previously positioned in the vessel until the cannula enters the vessel and a flashback of blood is observed whereby it may be determined that the plug is positioned proximal to the puncture site. The method includes the additional step of depositing the plug in a position proximal to the puncture site. Finally, the method includes the step of withdrawing the guidewire in the cannula from the puncture site.

As a result, the present invention provides a device which is capable of accurately and consistently delivering a vascular plug to the site of a puncture in a blood vessel, thereby ensuring complete hemostasis of an arterial puncture following a catherization procedure. The ability to control bleeding following a catherization procedure allows physicians to employ larger-sized catheters and/or more aggressive blood-thinning drugs. In addition, the present invention provides a technique that overcomes the drawbacks associated with the manual compression technique commonly employed by medical personnel. Finally, the present invention provides a device which can accomplish the task of delivering a plug to a puncture site with minimum additional intrusion to the blood vessel itself.

BRIEF DESCRIPTION OF THE DRAWINGS

FIG. 3 is an exploded perspective view of the delivery system of FIG. 1;

FIG. 4 is a cross-sectional view taken along lines 4—4 of FIG. 5;

FIG. 5 is a view, in partial section, of the delivery system in its delivery position;

FIGS. 6-8 illustrate one preferred technique of placing the vascular plug;

FIGS. 9-11 illustrate a second preferred technique for placing the vascular plug;

FIGS. 12-14 illustrate a third preferred technique for placing the vascular plug.

DETAILED DESCRIPTION OF THE INVENTION

Figure 1:
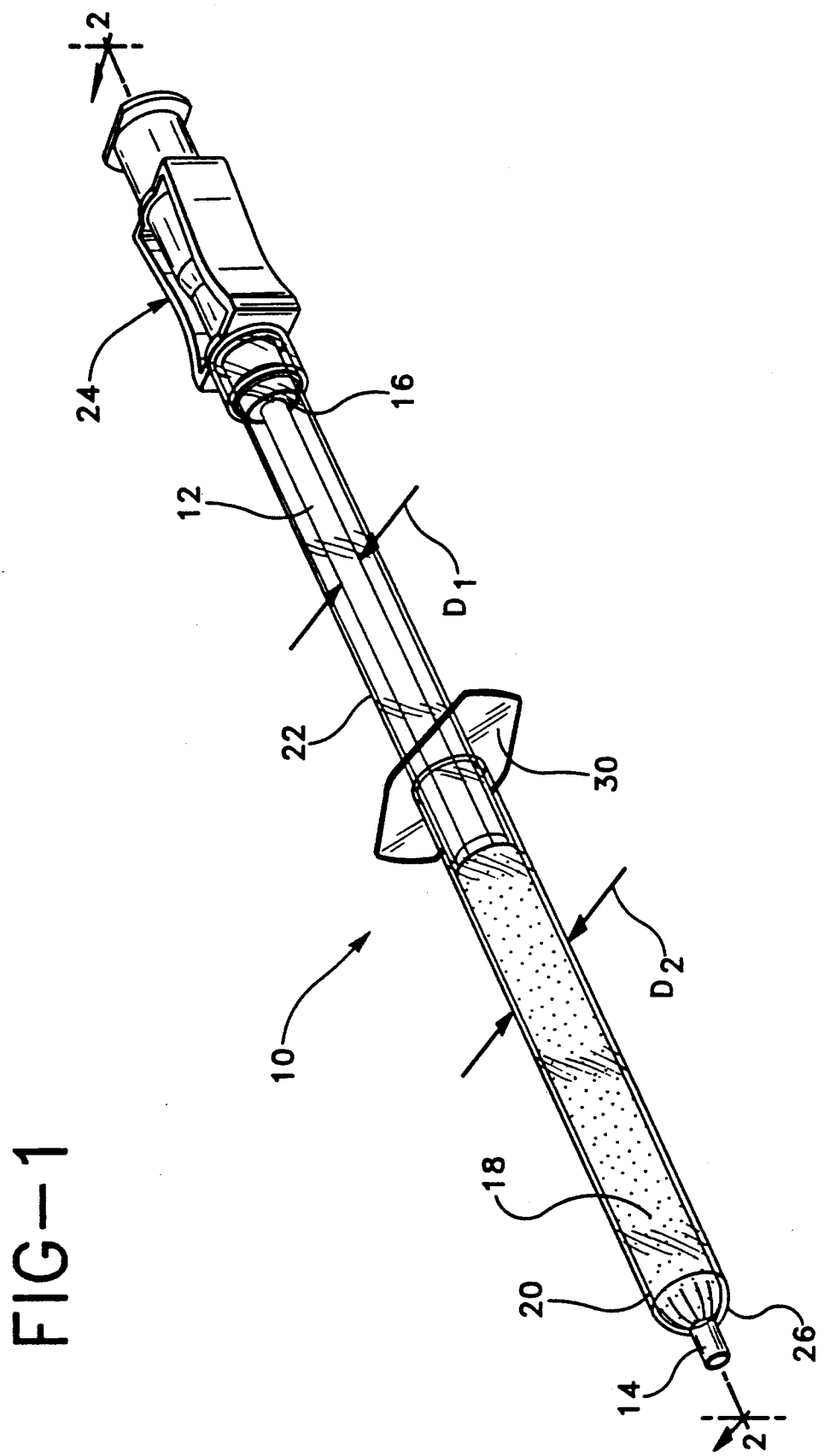
FIG. 1 is a perspective view of the delivery system according to the present invention.

Referring to the drawings and, in particular, to FIG. 1, a vascular plug delivery system 10 is shown. System 10 includes a cannula 12 having a tip portion 14 and a rear portion 16. A vascular plug 18 is disposed around the outside diameter of cannula 12 (proximal the tip portion) and, in turn, is enclosed by a housing 20. System 10 also includes a plug retaining tube 22 positioned rearward of the vascular plug. Finally, attached to the rear portion of cannula 12 is a hub assembly 24.

Vascular plug 18 may be of an expandable design, i.e., it tends to expand outward upon withdrawal of the housing, thereby ensuring complete hemostasis of the puncture. The plug may also be formed from a spongy or compressed material that expands upon contact with moisture in the body. Preferably, the plug is manufactured from a synthetic or natural resorbable material so that it is absorbed by the patient's body as the affected area heals. In this regard, one preferred material for manufacturing vascular plugs is collagen. Other materials such as synthetic biopolymers are also contemplated.

As will be described further below, the inside diameter of cannula 12 is dimensioned to pass over a guidewire (e.g., a guidewire remaining in a patient's blood vessel following a catheterization procedure). In this regard, the front end portion of housing 20 is provided with closures 26, which are designed and configured to enclose and protect the plug during the insertion of system 10 into the patient and also to facilitate entry of the system by smoothly dilating the tissue channel from a diameter $D_1$ corresponding to the cannula to a diameter $D_2$ corresponding to the housing.

Closures 26 are designed to open upon the application of a force. More particularly, when housing 20 is drawn rearward toward hub assembly 24, closures 26 will circumferentially open and coaxially align themselves with the outside diameter of housing 20 (see FIGS. 6-8 and 10-14), thereby allowing for withdrawal of the housing which, in turn, exposes the plug. Alternatively, housing 20 may be manufactured as a continuous tubular body, that is, without closures 26. In such an embodiment, the front end of the plug would be exposed to fluid during the placement procedure.

Figure 2:
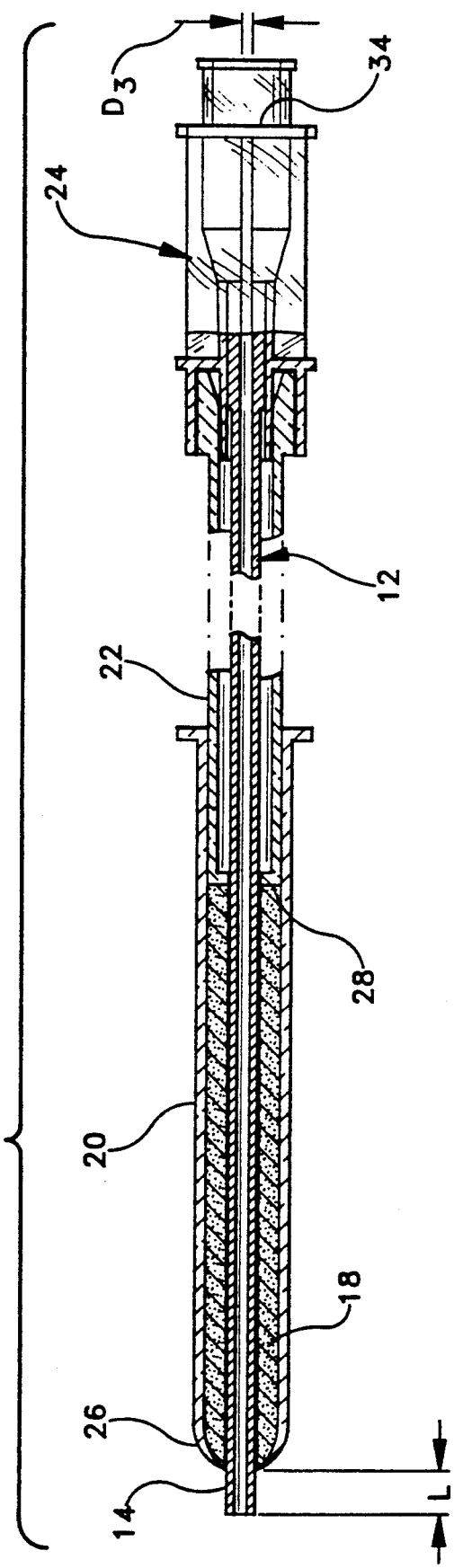
FIG. 2 is a cross-sectional view taken along lines 2—2 of FIG. 1.

Referring to FIG. 2, it can be seen that retaining tube 22 is dimensioned such that it is capable of sliding within housing 20. In this regard, front face 28 of retaining tube 22 (as best shown in FIG. 3) rests against the rearward surface of vascular plug 18. In such a configuration, retaining tube 22 acts to secure plug 18 in position while housing 20 is drawn rearward toward the hub assembly. To facilitate withdrawal of the housing, it may be provided with a flange 30 secured to its rearward end.

Referring to FIGS. 2-3, cannula 12 includes a continuous passageway 32 that extends for the substantial length of the delivery system. More particularly, the passageway extends from tip portion 14 to a point proximal surface 34 of hub assembly 24. Passageway 32 has a diameter $D_3$.

As previously mentioned, following a catheterization or similar procedure, it is necessary to control the bleeding from the puncture in the blood vessel. One technique for controlling this bleeding involves position-ing a vascular plug proximal the puncture. However, because of the working environment (blood vessels may move or twist, the tissue channel may close, etc.) it is difficult to ensure that a plug has been properly positioned proximal the puncture in the vessel. In this regard, it has been suggested to employ the guidewire remaining in the blood vessel following the catheterization procedure as a means of advancing the plug to the puncture. Still, even employing the guidewire, it can be difficult to ensure that the plug has been properly positioned (especially if the guidewire must be removed in order to deliver the plug).

A physician that employs only a guidewire will be forced to rely strictly on tactile sensation to position the plug. In other words, the physician is relying on "feel" to determine whether the plug is in the proper position. This can prove to be quite difficult in the situation where, for example, a large diameter catheter has been employed whereby a relatively large puncture exists in the vessel. In such a situation, the tactile sensation transmitted to the physician when the plug or delivery device contacts the vessel can be quite minimal, thereby creating the risk that the physician may actually deliver the plug in the blood vessel itself. Alternatively, the physician may deliver the plug at a point along the tissue channel, but at a distance away from the puncture, thereby creating the possibility that the vessel will continue to bleed into the surrounding tissues.

To guide the physician in positioning a vascular plug following a catheterization procedure, it has been discovered that a "flashback" technique can be employed. More specifically, it has been discovered that the blood flowing through the vessel can be utilized as an indicator to ensure that the plug is properly positioned in the patient prior to delivery of such plug.

The novel delivery system of the present invention has been designed to take advantage of this discovery. In particular, delivery system 10 has been provided with a cannula configured to pass over a previously-positioned guidewire. In addition, tip portion 14 of cannula 12 is of a length L. Tip portion 14 preferably has a length on the order of 2-6mm and is configured to pass through the puncture and enter the blood vessel. The passageway of cannula 12 is dimensioned (with respect to the guidewire) to allow a "flashback" of blood to exit the hub assembly.

Referring to FIG. 4, this "flashback" is accomplished by carefully sizing both passageway 32 and guidewire 36 to form a flow space 38 when delivery system 10 is advanced over the guidewire. Flow space 38 must be carefully sized to ensure that flashback occurs at the appropriate time. Specifically, if flow space 38 is too large, blood will tend to flashback as the delivery system is being advanced into the patient (i.e., before the tip portion of the cannula enters the vessel). On the other hand, if flow space 38 is too small, there may be no flashback of blood at all. Accordingly, the ratio between the diameter of the guidewire and the diameter of the passageway in the cannula must be such that flashback of blood will occur at the hub assembly (due to the pressure in the vessel) as the tip portion of the cannula enters the vessel. For example, the ratio may be from about 1:1.1 to 1:1.7 and, preferably, is about 1:1.35.

System 10 is shown in its delivery position in FIG. 5. In particular, the system is advanced into the tissue channel until tip portion 14 enters blood vessel 40. At this point, a flashback of blood will exit the rear of the hub assembly. The flashback informs the physician that the plug is properly positioned for delivery. The introducing of system 10 into the tissue channel until flashback occurs (as illustrated in FIG. 5), represents the first step in the placement procedure.

Following introduction of the delivery system into the tissue channel, various plug placement techniques can be employed. For example, one such technique is illustrated in FIGS. 6-8. Referring to FIG. 6, the housing is withdrawn outwardly from the tissue channel, thereby exposing the plug to the surrounding tissue. The plug, once the housing is withdrawn, tends to expand outwardly, thereby pressing against and closing the puncture in the vessel. The plug will tend to swell most in the region proximal to the puncture, i.e., the region where most of the blood is concentrated. Next, guidewire 36 is withdrawn from both the vessel and the delivery system. Removing the guidewire will allow a large amount of flashback to occur, thereby confirming to the physician that the plug remains properly positioned. As shown in FIG. 7, the cannula is then withdrawn from the tissue channel. As the cannula is withdrawn, retaining tube 22 is employed to maintain the plug securely in position, thereby preventing the plug from being "dragged" outward with the cannula or laterally moved. The plug, once the cannula is withdrawn, tends to expand inwardly, thereby closing the central lumen in the plug and sealing the vessel. Referring to FIG. 8, the final step in the first placement technique involves withdrawing the retaining tube from the tissue channel.

Figure 11:
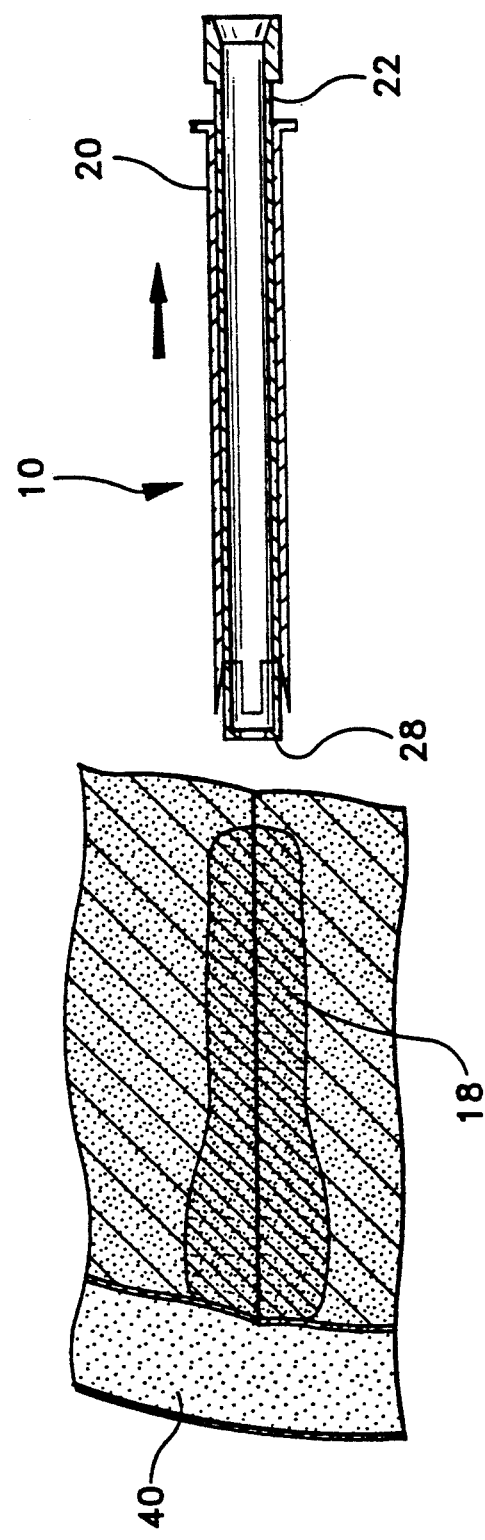

FIGS. 9-11 depict a second placement technique. Following the introduction of the delivery system (as shown in FIG. 5), both the guidewire and the cannula are withdrawn from the tissue channel (see FIG. 9) releasing the internal diameter of the plug and allowing it to expand inwardly, thereby closing the central lumen in the plug. Next, housing 20 is withdrawn from the tissue track, thereby exposing the plug. As the housing is being withdrawn, retaining tube 22 is employed to secure the plug in position. As mentioned above, the plug expands outward against the puncture in the vessel, providing hemostasis of the arterial puncture. Finally, as shown in FIG. 11, the retaining tube is withdrawn from the tissue channel.

Figure 14:
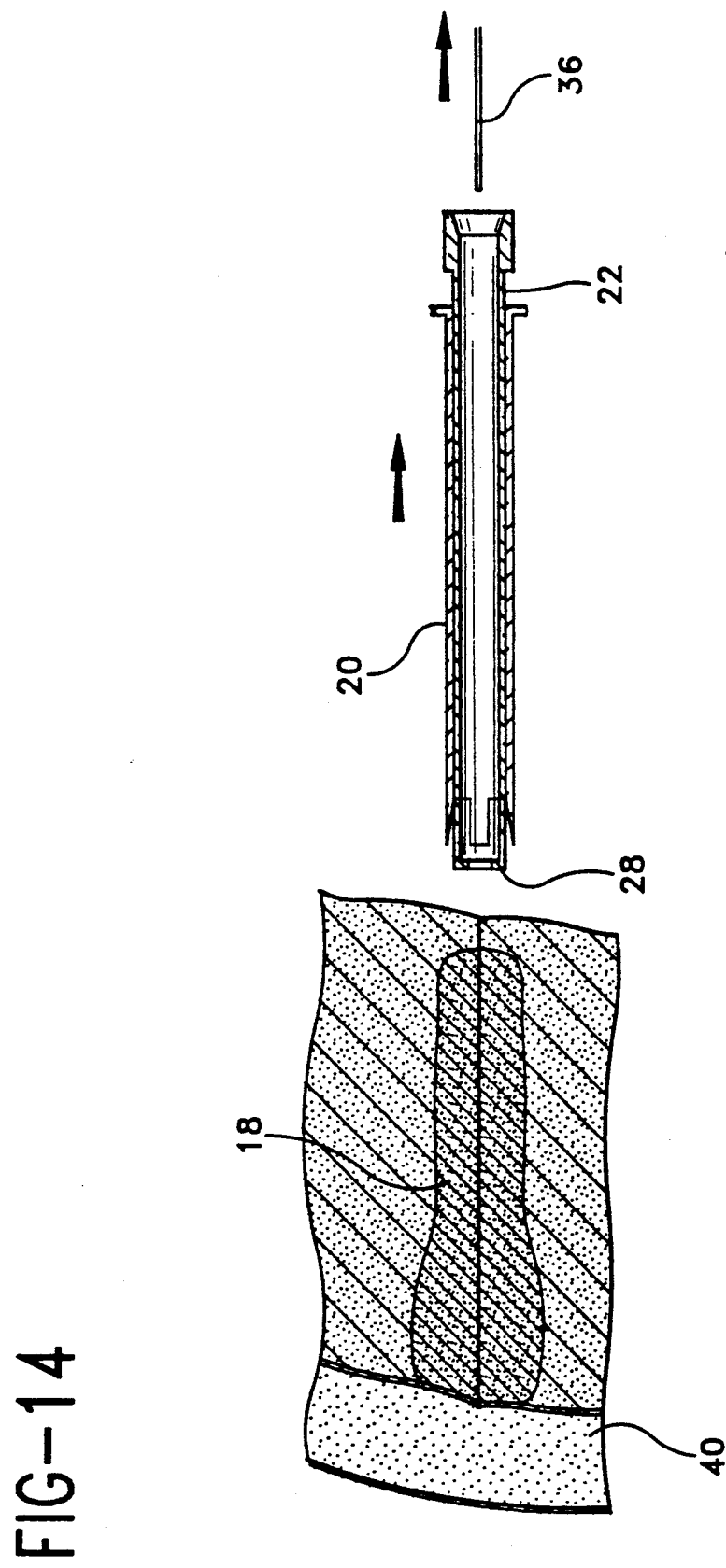

A third placement technique is depicted in FIGS. 12-14. Following the introduction of the delivery system (as shown in FIG. 5), housing 20 is withdrawn from the tissue channel, thereby exposing the plug and allowing outward expansion (see FIG. 12). The next step, as shown in FIG. 13, involves the withdrawal of the cannula, allowing inward expansion of the plug. Finally, the guidewire is withdrawn, allowing complete inward expansion of the plug. The retaining tube is then removed from the tissue channel.

Figure 15:
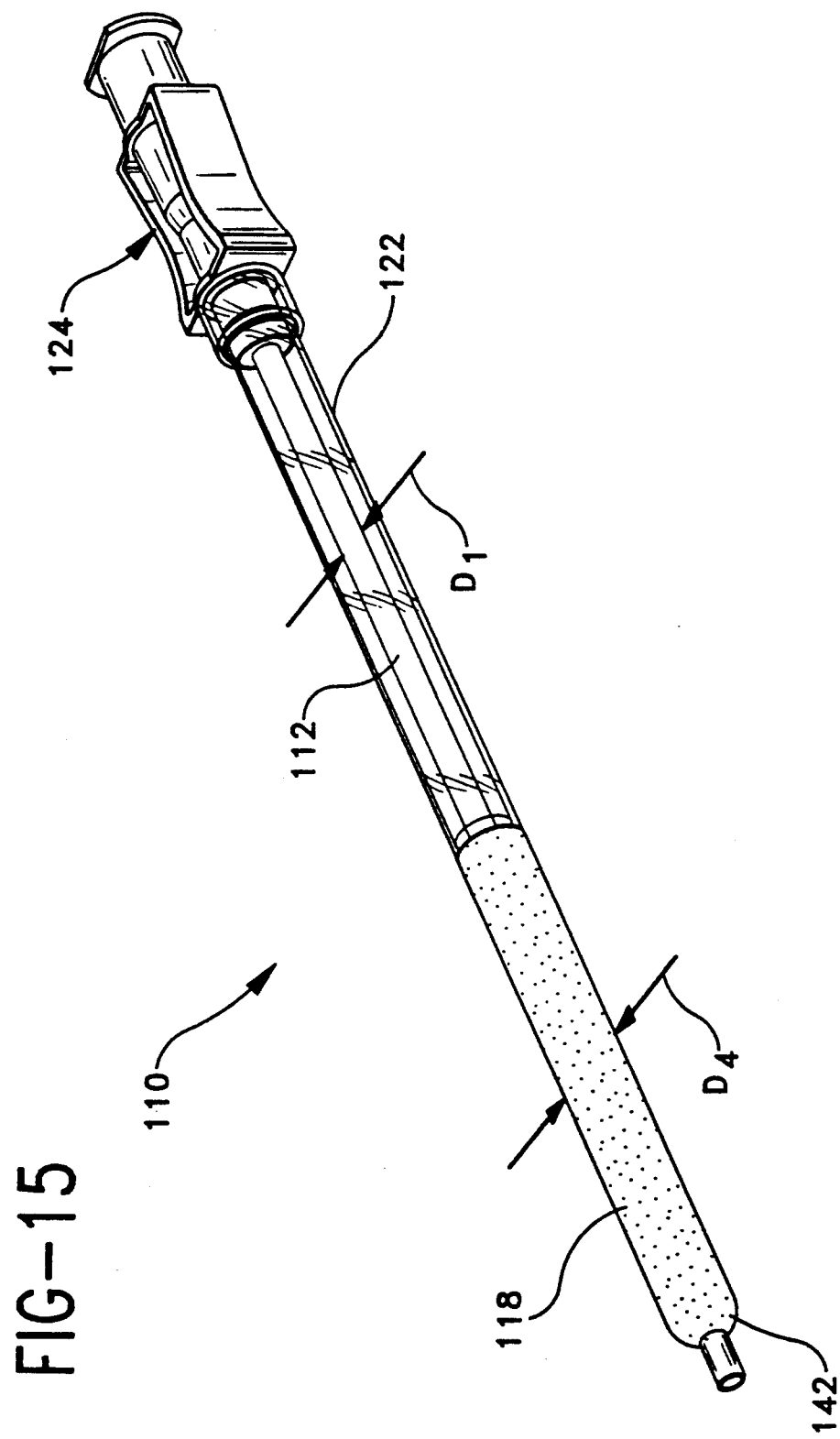
FIG. 15 is a perspective view of an alternative embodiment of the present invention.

An alternative embodiment of the present invention, i.e., delivery system 110, is illustrated in FIG. 15. Similar to delivery system 10, system 110 includes cannula 112, plug retaining tube 122 and hub assembly 124. Delivery system 110, however, does not employ a housing. Instead, the system employs an alternative vascular plug, i.e., plug 118, that is configured to facilitate introduction of the device into the patient absent the housing. In particular, plug 118 is formed with a smoothly-curved forward end 142 which facilitates introduction of the device by gradually dilating the tissue track from diameter $D_1$ to a diameter $D_2$. Further, the plug, in this embodiment, may be provided with a lubricous coating to facilitate the insertion process. Alternatively, the plug may be provided with a more densely packed material on the outside such that complete swelling of the plug occurs after it reaches the puncture site.

Plug 118 is positioned for delivery over the outside diameter of cannula 112. In this regard, it is necessary to secure the plug in its delivery position during introduction of the device. This may be accomplished in any number of ways, e.g., the plug may be removably secured on the cannula by friction, it may be removably secured on the cannula via an adhesive on the cannula or it may be removably secured via an adhesive or other interlocking means positioned between the rearward end of the plug and front face 128.

Figure 16:
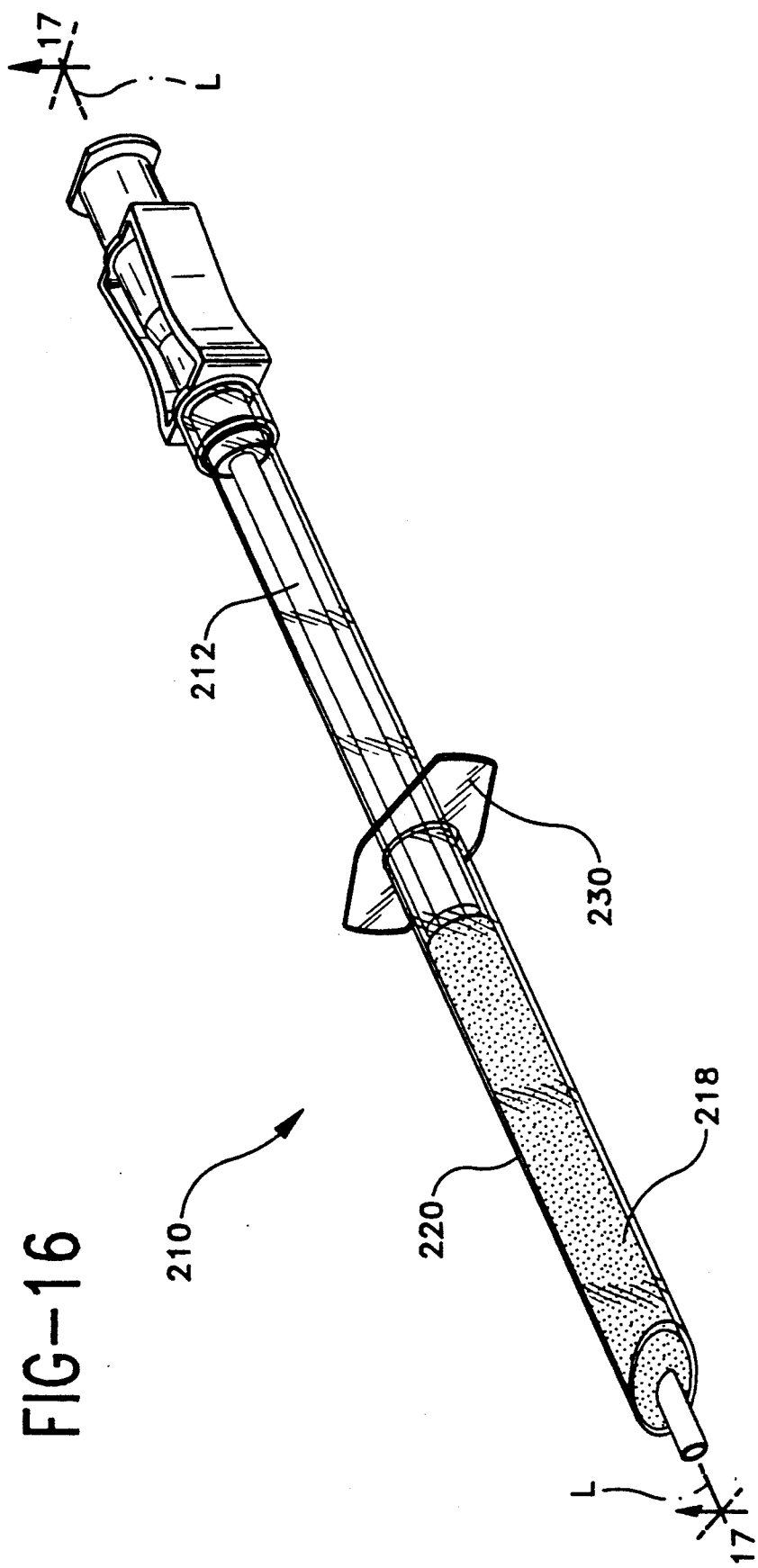
FIG. 16 is a perspective view of another alternative embodiment of the present invention.
Figure 17:
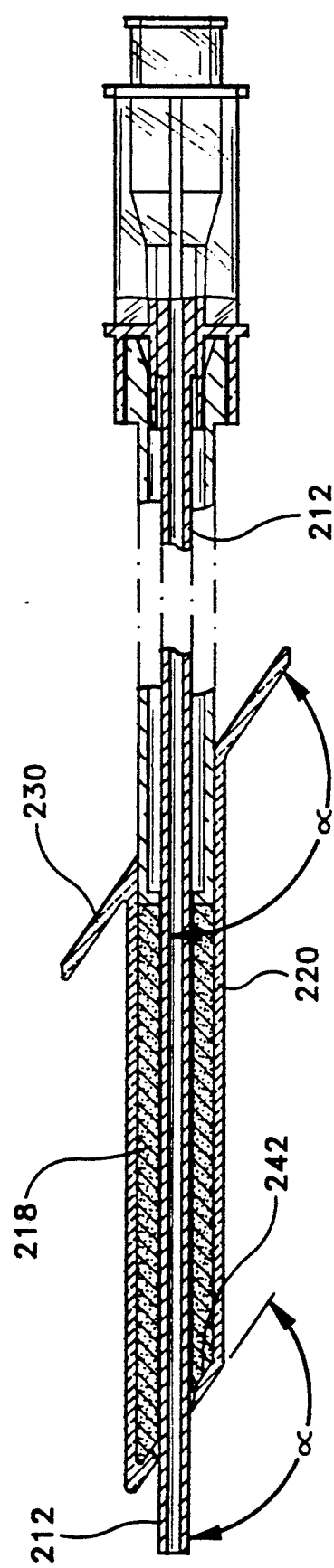
FIG. 17 is a cross-sectional view taken along lines 17—17 of FIG. 16.

Another embodiment of the present invention, i.e., 1 delivery system 210, is shown in FIGS. 16–17. System 210 differs from system 10 in that the forward end of housing 20 is beveled at an angle α with respect to axis L extending through cannula 212. Similarly, flange 230 is beveled at angle α with respect to axis L. In turn, forward end 242 of plug 218 is also beveled at angle α. Angle α is preferably from about 120° to 135°. Finally, housing 220 may or may not be fabricated with closures 26.

Figure 18:
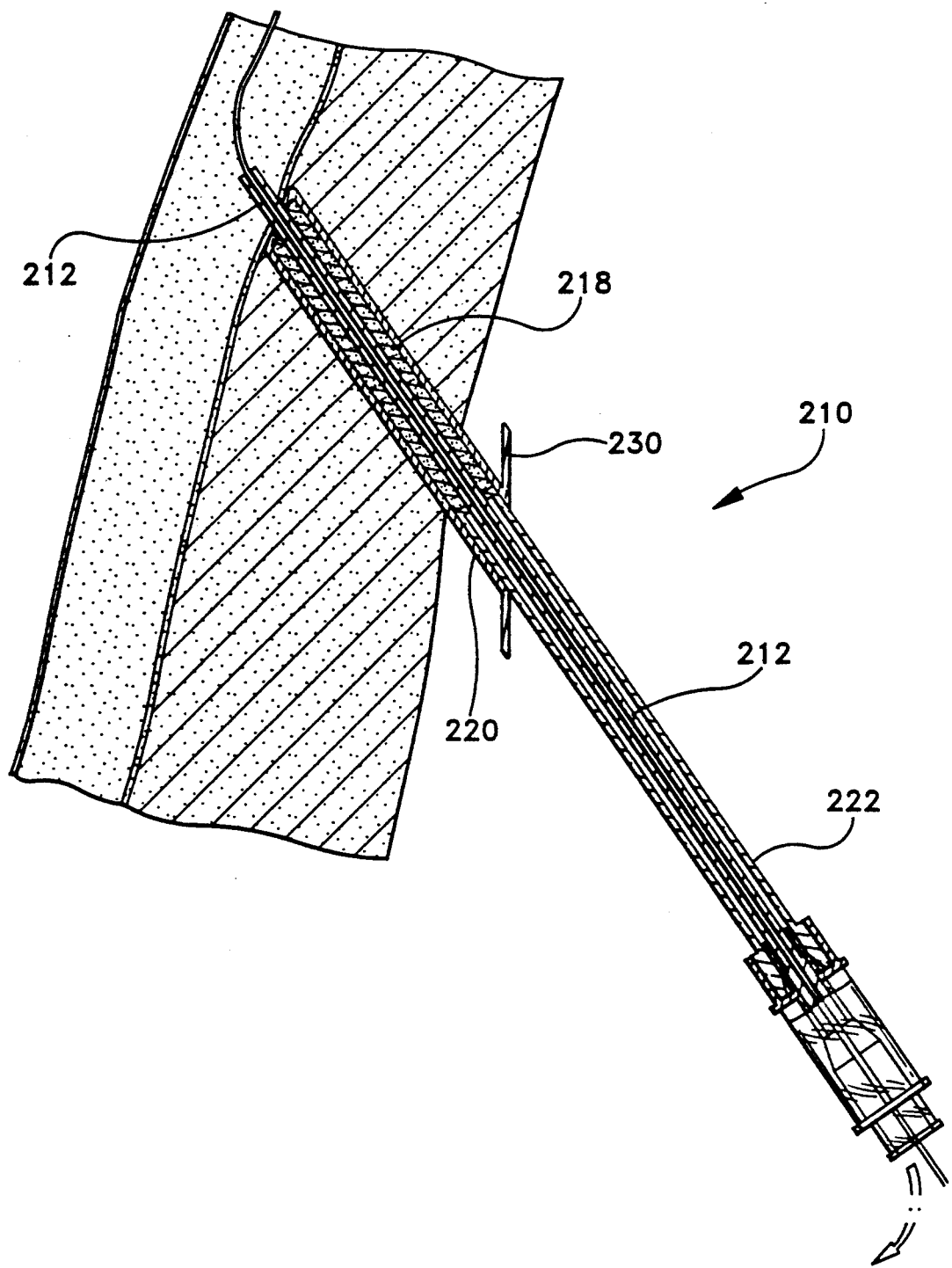
FIG. 18 is a perspective view, in partial section, of the delivery system of FIG. 16 in its delivery position.

An advantage associated with system 210 is illustrated in FIG. 18. Specifically, many, if not all, arterial punctures are performed at an angle from about 30° to 45° with respect to the artery. Referring to FIG. 18, it can be seen that by bevelling the forward end of the housing and plug, a larger surface area of plug can be positioned at the puncture. Moreover, the system 210 ensures that the forward end of the plug is delivered in a more parallel fashion to the vessel puncture site. Finally, the flange, which is oriented parallel to the forward end of the plug, provides an external visible guide to the physician that assists the physician in positioning the plug face in parallel arrangement to the vessel.

EXAMPLES

A domestic swine (approximately 100–125 pounds) was anesthetized and the groin area aseptically prepared for percutaneous arterior puncture. The left femoral artery was punctured and a 0.035" guidewire was advanced therein.

The distance from the skin surface to the artery wall was between 15–19mm, depending on the reference point on the needle (Bevel heel -15mm; Bevel tip - 19mm; Lumen Axis - 17mm). The artery was thereafter dilated using a standard dilator. Cannulas having internal diameters of various sizes were then advanced over the guidewire until either flashback occurred or the physician determined through tactile sensation that the cannula tip had entered the blood vessel. At this point, the insertion depth of the cannula was measured (to later be compared with the initial 15–19mm measurement).

|  | 18 Gauge 9.6 Fr System (.039" ID) | 17 Gauge 9.6 Fr System (.047" ID) | 15 Gauge 11.4 Fr System (.059" ID) |
|---|---|---|---|
| Example 1 The site was dilated to 9 French. | | | |
| Flashback: | Slight | Strong | Good |
| Depth: | 16.8 mm | 16.5 mm | 12 mm |
| Tactile Sensation: | Yes (Strong) | Yes (Good) | Yes (Fair) |
| Example 2 The site was dilated to 10 French. | | | |
| Flashback: | Slight | Good | Good |
| Depth: | 30 mm | 16 mm | 11 mm |
| Tactile Sensation: | No | Yes (Good) | Yes (Fair) |
| Example 3 The site was dilated to 12 French. | | | |
| Flashback: | Slight | Good | Good |
| Depth: | 29.5 mm | 23.5 mm | 14 mm |
| Tactile Sensation: | No | Yes (Fair) | Yes (Fair) |

The 17 Gauge 9.6 Fr system generated flashback when advanced over an 0.035" guidewire to a depth substantially equal to that previously measured (i.e., the distance from the skin surface to the arterial surface). The increase in this depth to 23.5mm after dilation to 12Fr was due to a hematoma that was spreading from the site of the puncture.

While there have been described what are presently believed to be the preferred embodiments of the invention, those skilled in the art will realize that various changes and modifications may be made to the invention without departing from the spirit of the invention, and it is intended to claim all such changes and modifications which fall within the scope of the invention.

What is claimed is:

1. A device for in vivo delivery of a vascular plug to a site of a puncture in a blood vessel in which a guidewire has been inserted, comprising:
   a cannula capable of passing over a guidewire and having sufficient length and dimension to enter a blood vessel puncture;
   a vascular plug disposed in a delivery position over the outside diameter of said cannula; and
   means carried by the cannula for retaining said plug at a vessel puncture site during withdrawal of said cannula from the site of the puncture.

2. The device according to claim 1, wherein said cannula is introduced into said blood vessel through a tissue channel, and wherein said plug has a shaped forward end which facilitates introduction of said device by gradually dilating said tissue channel from a diameter corresponding to said cannula to a diameter corresponding to said plug.

3. The device according to claim 2, wherein said plug is provided with a coating for facilitating entry of said device.

4. The device according to claim 2, wherein said plug is made of a swellable material.

5. The device according to claim 2, wherein said plug is made of a compressible material.

6. The device according to claim 2, wherein said plug is made of a resorbable material.

7. The device according to claim 2, wherein said plug is made of collagen.

8. The device according to claim 1, further comprising a guidewire, and wherein said guidewire has an outside diameter less than the inside diameter of said cannula whereby flashback of blood occurs in a flow space between said guidewire and said cannula when said cannula enters said puncture.

9. The device according to claim 8, wherein the ratio between the outside diameter of said guidewire and the inside diameter of said cannula is from about 1:1.1 to 1:1.7.

10. The device according to claim 9, wherein the ratio between the outside diameter of said guidewire and the inside diameter of said cannula is about 1:1.35.

11. The device according to claim 10, wherein said guidewire has an outside diameter of about 0.035 inches.

12. A device for in vivo delivery of a vascular plug to a site of a puncture in a blood vessel in which a guidewire has been inserted, comprising:
    a cannula capable of passing over a guidewire and having sufficient length and dimension to enter a blood vessel puncture;
    a vascular plug disposed in a delivery position over the outside diameter of said cannula;
    a housing adapted to slide over said cannula and having sufficient space therein to accommodate said vascular plug; and
    means carried by the cannula for retaining said plug at a vessel puncture site during withdrawal of said housing and said cannula from said site.

13. The device according to claim 12, wherein said housing is configured to protect and facilitate delivery of said plug during delivery.

14. The device according to claim 13, wherein said housing includes a front end portion designed to open upon the application of force thereto and allow delivery of said plug to said vessel puncture site.

15. The device according to claim 14, wherein said front end is beveled at an angle with respect to an axis passing through said cannula.

16. The device according to claim 14, wherein said housing includes a flange attached to its rearward end to facilitate withdrawal of said housing.

17. The device according to claim 12, wherein said means for retaining is a plug retaining tube concentric with and circumferentially surrounding said cannula.

18. The device according to claim 17, wherein said retaining tube has an outside diameter less than the inside diameter of said housing so that said retaining tube may slide within said housing and contact said plug.

19. The device according to claim 12, wherein said vascular plug is manufactured from a material that expands outward upon release from said housing.

20. The device according to claim 12, wherein said vascular plug is manufactured from an resorbable material.

21. The device according to claim 12 wherein said vascular plug is made of collagen.

22. The device according to claim 12, further comprising a hub assembly connected to the rear portion of said cannula.

23. The device according to claim 12, further comprising a guidewire, and wherein said guidewire has a diameter less than the inside diameter of said cannula whereby flashback of blood occurs when said cannula enters said puncture.

24. The device according to claim 23, wherein the ratio between the outside diameter of said guidewire and the inside diameter of said cannula is from about 1:1.1 to 1:1.7.

25. The device according to claim 24, wherein the ratio between the outside diameter of said guidewire and the inside diameter of said cannula is about 1:1.35.

26. The device according to claim 25, wherein said guidewire has an outside diameter of about 0.035 inches.

27. A method for in vivo delivery of a vascular plug to a site of a puncture in a blood vessel comprising:
advancing a cannula having a plug disposed over its outside diameter to a vessel puncture site over a guidewire previously positioned in said vessel until said cannula enters said vessel and a flashback of blood is observed whereby it may be determined that said plug is positioned proximal said vessel puncture site;
depositing said plug in a position proximal said vessel puncture site; and
withdrawing said guidewire and said cannula from said vessel puncture site.

28. The method according to claim 27, further comprising a housing adapted to slide over said cannula.

29. The method according to claim 28, wherein said housing surrounding said plug is first withdrawn from said vessel puncture site, and wherein said guidewire is thereafter withdrawn from said vessel puncture site, and wherein said cannula is thereafter withdrawn from said vessel puncture site.

30. The method according to claim 28, wherein said cannula is first withdrawn from said vessel puncture site, wherein said housing surrounding said plug is thereafter withdrawn from said vessel puncture site, and wherein said guidewire is thereafter withdrawn from said vessel puncture site.

31. The method according to claim 28, wherein said housing surrounding said plug is first withdrawn from said vessel puncture site, wherein said cannula is thereafter withdrawn from said vessel puncture site, and wherein said guidewire is thereafter withdrawn from said vessel puncture site.

* * * * *

UNITED STATES PATENT AND TRADEMARK OFFICE
CERTIFICATE OF CORRECTION

PATENT NO. : 5,320,639
DATED : June 14, 1994
INVENTOR(S) : Rudnick

It is certified that error appears in the above-indentified patent and that said Letters Patent is hereby corrected as shown below:

In Col. 6, line 55,      "diameter $D_2$" should be --diameter $D_2$.--;

In Col. 7, line 3,       "i.e., 1" should be --i.e.,--; and

In Col. 7, line 6,       "housing 20" should be --housing 220--.

Signed and Sealed this

First Day of November, 1994

*Attest:*

BRUCE LEHMAN

*Attesting Officer*      *Commissioner of Patents and Trademarks*